United States Patent
Ohlbach et al.

(12)

(10) Patent No.: US 6,348,601 B2
(45) Date of Patent: Feb. 19, 2002

(54) PREPARATION OF N-METHYL-2-PYRROLIDONE (NMP)

(75) Inventors: Frank Ohlbach, Dossenheim; Johann-Peter Melder, Böhl-Iggelheim; Karl-Heinz Ross, Grünstadt; Martin Rudloff, Weisenheim, all of (DE); Jörg Liebe, Tokyo (JP)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/774,628

(22) Filed: Feb. 1, 2001

(30) Foreign Application Priority Data

Feb. 4, 2000 (DE) .......................................... 100 04 909

(51) Int. Cl.$^7$ .......................................... C07D 207/267
(52) U.S. Cl. ...................................... 548/552
(58) Field of Search .......................................... 548/552

(56) References Cited

FOREIGN PATENT DOCUMENTS

| JP | 47-018751 | 5/1972 |
| JP | 1186-863 | 7/1989 |
| JP | 1186-864 | 7/1989 |
| JP | 1190-667 | 7/1989 |
| JP | 10-158238 | 6/1998 |

OTHER PUBLICATIONS

Ramioulle et al. "Improved Methylamines Process" Hydrocarbon Process (1981) pp. 113–117.
Kirk Othmer, Encyclopedia of Chemical Technology vol.2, (1992) pp. 373–376.
Weissermel et al. "Industrielle Organische Chemie" (1990) pp. 53–54.
Ullmann's Encyclopedia of Industrial Chemistry vol. A16 (1990) pp. 535–541.
Ullmann's Encyclopedia of Industrial Chemistry vol. A22(1993) pp. 458–459.

*Primary Examiner*—Floyd D. Higel
*Assistant Examiner*—Donna N. Wright
(74) *Attorney, Agent, or Firm*—Keil & Weinkauf

(57) ABSTRACT

N-Methyl-2-pyrrolidone (NMP) is prepared by preparing a mixture comprising monomethylamine, dimethylamine and trimethylamine and ammonia in a first process step by reacting ammonia with methanol at elevated temperature in the presence of a catalyst, separating 10 off the ammonia, reacting the mixture comprising the methylamines with gamma-butyrolactone (γ-BL), in a molar ratio of monomethylamine to γ-BL of at least 1 in a second process step at elevated temperature and superatmospheric pressure, separating NMP and unreacted methylamines from the reaction product and returning unreacted methylamines to the first process step for reaction with methanol and ammonia.

8 Claims, No Drawings

PREPARATION OF N-METHYL-2-PYRROLIDONE (NMP)

The present invention relates to a process for preparing N-methyl-2-pyrrolidone (=1-methyl-2-pyrrolidinone, NMP)

Owing to its ready volatility, thermal stability, high polarity and aprotic properties, NMP is suitable as a solvent for polymers and as a solvent for numerous organic syntheses, e.g. alkylations or preparation of carboxylic acids and their derivatives.

NMP is industrially important for, in particular, the separation of acetylene from cracker gas or of butadiene from $C_4$ fractions, for the extraction of aromatics or for the absorption of acidic constituents in gas scrubbers.

The industrial preparation of NMP is predominantly carried out by reaction of gamma-butyrolactone (γ-BL) with monomethylamine (MMA) in a tube reactor, e.g. a shaft reactor, at from 200 to 350° C. and superatmospheric pressure, e.g. about 10 MPa (Ullmann's Encyclopedia of Industrial Chemistry, $5^{th}$ ed, Vol. A22, pages 458 to 459 (1993)).

For example, JP-A-10 158 238 (Derwent Abstr. 98-393443/34) describes the reaction of γ-BL with excess MMA at from 250 to 300° C. in the presence of water to form NMP.

JP-A-1 190 667 (Derwent Abstr. 89-260914/36) describes the preparation of NMP by reaction of γ-BL with excess MMA, with the MMA remaining unreacted after the reaction and also the dimethylamine (DMA) and trimethylamine (TMA) obtained as by-products together with added water are returned to the reaction of γ-BL with excess MMA.

JP-A-7 218 751 (Derwent Abstr. 35795T-E) reports the synthesis of NMP by heating γ-BL or open-chain derivatives thereof with DMA and/or TMA at above 200° C. In an example, the reaction of γ-BL with aqueous DMA at 270° C./3 h gives NMP in a yield of 80%.

JP-A-1 186 864 (Derwent Abstr. 89-259000/36) discloses the preparation of N-alkylated lactams by reaction of the corresponding lactones with secondary amines in the presence of water via the corresponding N,N-dialkyl-omega-hydroxycarboxamides as intermediates. According to Example 1 of this patent application, the reaction of γ-BL with aqueous DMA gives an NMP yield of 60% and additionally forms methylamides of γ-hydroxybutyric acid. In the single further example according to the application, too, an NMP yield of 60% is reported for the corresponding reaction of γ-BL with DMA.

JP-A-1 186 863 (Derwent Abstr. 89-258999/36) describes the preparation of N-alkylated lactams by reaction of corresponding lactones with tertiary amines or with tertiary or quaternary ammonium compounds in the presence of water with elimination of a corresponding alcohol. According to Example 1 of this patent application, the reaction of γ-BL with aqueous TMA gives an NMP yield of 8% and forms large amounts of by-products such as methylamides of γ-hydroxybutyric acid, 2-pyrrolidone and γ-hydroxybutyric acid.

The methylamines monomethylamine (MMA), dimethylamine (DMA) and trimethylamine (TMA) are prepared industrially in a continuous process by (exothermic) reaction of ammonia with methanol in the presence of a catalyst at elevated temperature (e.g.; Kirk-Othmer, Encyclopedia of Chemical Technology, $4^{th}$ ed., Vol. 2, pages 373 to 375 (1992) and Ullmann's Encyclopedia of Industrial Chemistry, 5th Ed., Vol. A16, pages 535 to 541 (1990)).

Catalyst used are acid catalysts, in particular solid acid catalysts such as silicon oxides (silica, $SiO_2$), aluminum oxides (alumina, $Al_2O_3$), silica-alumina ($Sio_2.Al_2O_3$), titanium oxides (titania, $TiO_2$), tungsten oxides, phosphates ($AlPO_4$), zeolites and clays (method 1) or metal catalysts such as cobalt-, nickel- or copper-containing catalysts (e.g. copper chromite) (method 2). The catalyst is usually installed as a fixed bed.

The reaction temperatures in method 1 are generally from 300 to 500° C., in particular from 390 to 430° C., and the reaction temperatures in method 2 are generally from 130 to 250° C.

In method 1, the pressure is generally from 790 to 3550 kPa, in particular from 1500 to 3000 kPa; method 2 is usually carried out in the presence of hydrogen.

In these reactions of ammonia with methanol, a mixture of the methylamines MMA, DMA and TMA together with water is always obtained. The total selectivity to the methylamines is about 94%, secondary reactions are dissociations to form CO, $CO_2$, $CH_4$, $H_2$ and $N_2$ (cf., for example, K. Weissermel et al., Industrielle Organische Chemie, $3^{rd}$ edition, pages 53 to 54 (1990)).

The crude reaction product comprising essentially ammonia, water, possibly unreacted methanol and the methylamines is fractionated by means of a continuous multistage, technically complicated distillation (combination of various pressure distillations and extractive distillations). A typical process diagram for the synthesis of methylamines and their isolation is shown in FIG. 2 in Kirk-Othmer, Encyclopedia of Chemical Technology, $4^{th}$ ed., Vol. 2, pages 375 (1992), which is hereby incorporated by reference.

For example, in a distillation sequence which is technically complicated overall, ammonia and part of the TMA is firstly separated from the reaction mixture and the remaining TMA is subsequently separated off in an extraction column using water. Ammonia is returned to the reaction. In a subsequent dewatering column, MMA and DMA are separated off by the top and separated from one another in a separate column. Methanol is taken off at a side outlet of the dewatering column and separated from water in a separate column and returned to the synthesis. DMA and TMA can likewise be returned in principle to the reaction of $NH_3$ with methanol, with mixtures of MMA, DMA and TMA again being formed from DMA and TEA under the reaction conditions (thermodynamic equilibrium; cf, for example, Ullmann's Encyclopedia of Industrial Chemistry, $5^{th}$ ed., Vol. A16, page 537 (1990)).

Further configurations of the methylamine production process may be found in J. Ramioulle et al., Hydrocarbon Processing, July 1981, pages 113 to 117 (cf., for example, FIG. 6 on page 117 of this document), which is hereby likewise incorporated by reference.

A disadvantage of the processes of the prior art for preparing NM? from ammonia, methanol and γ-BL is that the MMA required for the reaction with γ-BL firstly has to be isolated from the crude reaction product from the synthesis of methylamines by means of a technically very complicated distillation cascade (plurality of distillation columns connected in series) (as described above).

It is an object of the present invention to overcome the disadvantages of the prior art by finding an efficient, selective, economical and technically less complicated process for preparing NMP in high yields (based on γ-BL) and high space-time yields from ammonia, methanol and γ-BL.

We have found that this object is achieved by a process for preparing N-methyl-2-pyrrolidone (NMP), which comprises preparing a mixture comprising monomethylamine, dimethylamine and trimethylamine and ammonia in a first process step by reacting ammonia with methanol at elevated temperature in the presence of a catalyst, separating off the ammonia, reacting the mixture comprising the methylamines with gamma-butyrolactone (γ-BL), in a molar ratio of monomethylamine to γ-BL of at least 1 in a second process step at elevated temperature and superatmospheric pressure, separating NMP and unreacted methylamines from the reaction product and returning unreacted methylamines to the first process step for reaction with methanol and ammonia.

According to the present invention, the technically very complicated fractionation of the crude reaction product from the reaction of methanol with ammonia to give the individual methylamines MMA, DMA and TMA or the corresponding binary mixtures (e.g. MMA+DMA) can be dispensed with.

The process of the present invention can be carried out as is follows:

Ammonia is reacted with methanol in the presence of an acid catalyst, particularly preferably a solid acid catalyst (e.g. AlO$_x$), or a metal catalyst, with the catalyst particularly preferably being installed in the reactor as a fixed bed, at elevated temperature according to the known methods of the prior art as have been described above to give a mixture consisting essentially of the three methylamines aMA, DMA and TMA, ammonia, water and possibly unreacted methanol. (First process step).

In this context, "essentially" means that the total content of the three methylamines, ammonia, water and, if present, methanol in the mixture is at least 95% by weight, preferably at least 97% by weight, in particular at least 98% by weight, particularly preferably at least 99% by weight.

Subsequently, in a distillation column, the ammonia is separated off via the top from the mixture consisting essentially of the three methylamines, ammonia, water and possibly unreacted methanol in accordance with known methods (cf., for example, FIG. 2. in Kirk-Othmer, Encyclopedia of Chemical Technology, 4$^{th}$ ed., Vol 2, page 375: first column after the reactor).

This gives a mixture consisting essentially of the three methylamines, water and possibly methanol. In this context, "essentially" means that the total content of the three methylamines, water and, if present, methanol in the mixture is at least 96% by weight, preferably at least 97% by weight, in particular at least 98% by weight, particularly preferably at least 99% by weight.

The water content of this mixture is generally from 30 to 50% by weight, preferably from 35 to 45% by weight.

The methanol content of this mixture is generally from 0 to 10% by weight, preferably from 3 to 7% by weight.

The residual ammonia content of this mixture is generally from 0 to 1% by weight, preferably from 0.1 to 0.8% by weight.

The weight ratio of the methylamines in this mixture is generally MMA:DMA:TMA=(1–14):(6–12):(0.2–12), preferably MMA DMA:TMA=(1–2.7):(2–3):(0.07–2).

In a subsequent extraction column and one or more distillation columns, any methanol and water present in this mixture can, if desired, be reduced in concentration or separated off at the top and bottom respectively according to known methods (cf., for example, FIG. 2. In Kirk-Othmer, Encyclopedia of Chemical Technology, 4$^{th}$ ed., Vol. 2, page 375: second and third columns after the reactor).

The mixture which is obtained after the above steps and consists essentially of the three methylamines MMA, DMA and TMA, possibly water and possibly methanol is reacted with gamma-butyrolactone (γ-BL) at elevated temperature, preferably at from 180 to 350° C., in particular from 200 to 300° C., particularly preferably from 230 to 270° C., and at superatmospheric pressure, preferably at from 5 to 300 bar, in particular from 50 to 150 bar. (Second process step)

The molar ratio of MMA to γ-BL here is at least 1, preferably at least 1.05, particularly preferably at least 1.1. Preferred ranges for the molar ratio of MMA to γ-BL are from 1 to 2, preferably from 1.05 to 1.5, particularly preferably from 1.1 to 1.25.

The reaction can be carried out batchwise in a pressure reactor (autoclave) or preferably continuously in a tube reactor which may be fitted with internals for influencing the flow behavior in the reactor, e.g. in a shaft reactor.

The residence time of the reaction mixture in the reactor under the conditions indicated is generally from 1 to 6 hours, preferably from 1.5 to 5 hours, particularly preferably from 2 to 4 hours.

For this reaction, preference is given to using a gamabutyrolactone (γ-BL) having a purity of at least 98% by weight, preferably at least 99% by weight.

The γ-BL required can be obtained by known methods by means of the endothermic cyclizing dehydrogenation of 1,4-butanediol in the gas phase over a metal catalyst (e.g. a copper catalyst) at elevated temperature or by means of selective hydrogenation of maleic anhydride at superatmospheric pressure and elevated temperature over a metal catalyst and, in each case, subsequent purification by distillation (Ullmann's Encyclopedia of Industrial Chemistry, 5$^{th}$ ed., Vol. A4, page 496 (1985)).

The reaction product obtained comprises NMP, unreacted methylamines (in particular unreacted DMA and TMA), water, small amounts of by-products, possibly methanol and possibly unreacted γ-BL.

In general, the γ-BL conversion in this process step under the reaction conditions indicated is greater than 95%, in particular greater than 97%, very particularly preferably greater than 99%.

The by-product content of the reaction product is typically less than 5% by weight, in particular less than 3.5% by weight, very particularly preferably less than 2% by weight.

The desired process product NMP is isolated from the reaction product by single-stage or multistage fractional distillation.

For example, the work-up of the reaction product by distillation can be carried out in two stages, with DMA and TMA and any MMA still present being taken off at the top as distillate in the first distillation stage and water being separated off at the top and the pure NMP being taken off at a side offtake in the second distillation stage.

The methylamines obtained in the work-up of the reaction product by distillation, in particular DMA and TMA, are, according to the present invention, returned to the first process step of reaction of ammonia with methanol.

Correspondingly, the methanol obtained can also be returned to the first process step.

In the process of the present invention, the selectivity for the formation of NMP (based on γ-BL) is greater than 90%, in particular greater than 93%, very particularly preferably at least 95%, at γ-BL conversions of greater than 95%.

Since it was known from the prior art that DMA and TMA also react with γ-BL, but in each case NMP is obtained only in very poor selectivities and yields because of the formation of by-products, it is surprising that the process of the present invention, in which MMA, DMA and TMA are reacted with γ-BL and unreacted methylamines are subsequently returned to the reaction of NHj with methanol, achieves very high selectivities and yields for the formation of VMP (based on γ-BL).

This fact is illustrated by Examples 1 to 4 below.

Examples 1 and 2 below show that in each case γ-BL reacts virtually quantitatively even at 5° C. to room temperature with aqueous solutions of the excess methylamine MWA and/or TMA to give the corresponding methylamides of γ-hydroxybutyric acid.

Example 2 shows that the amides obtained from γ-BL and MMA or DMA, namely γ-hydroxybutyric acid monomethylamide or γ-hydroxybutyric acid dimethylamide and the internal salt obtained from γ-BL and TMA even at room temperature ("TMA-BL adduct") of the formula

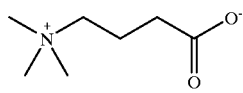

can be converted into NMP at elevated temperature, preferably at above 200° C., by cyclization and elimination of water or methanol.

According to the present invention, it was recognized that under comparable conditions the cyclization of the monomethylamide to NMP proceeds significantly more quickly than that of the dimethylamide or the TMA-BL adduct. It was also found that the cyclization to NMP can be carried out either in aqueous solution or in the absence of water. Under anhydrous conditions, the NMP yields starting from DMA or TMA are significantly lower than when the reactions are carried out in the presence of water (Examples 2a and 2b).

The yields of VMP obtained by reacting DMA or TMA with γ-BL at 255° C./3 h are, however, at most only 63% in Example 2. In these reactions with DMA or TMA, the γ-BL conversion is in each case significantly higher than the corresponding NMP yield, since considerable amounts of by-products such as γ-hydroxybutyric acid dimethylamide or TMA-BL adduct are present in the reaction product.

Furthermore, it was recognized according to the present invention (see Example 3) that γ-hydroxybutyric acid monomethylamide and γ-hydroxybutyric acid dimethylamide are very readily converted into one another in the presence of excess MMA or DMA at temperatures above about 80° C., i.e. a thermodynamic equilibrium between the two amides is established at elevated temperature.

In addition, it was recognized according to the present invention (Example 4) that the reaction of an equimolar mixture of MMA and DMA with a molar excess of γ-BL (based on MMA+DMA), where MMA is present in an at least equimolar amount based on γ-BL, initially forms a mixture of the two corresponding amides (hydroxybutyric acid monomethylamine and γ-hydroxybutyric acid dimethylamide) in a ratio of about 3:1 (with the monomethylamide being the major component) at room temperature in a kinetically controlled reaction. Increasing the temperature to above 80° C. results in establishment of the thermocynamic equilibrium between the two corresponding amides, which is even more distinctly on the side of the monomethylamide At 270° C., the ratio shifts to about 4:1 (again with the monoamide as major component)

EXAMPLES

Example 1

Preparation of the Open-chain Amides from γ-BL and MMA or DMA

The reactions were carried out in a round-bottomed flask with ice cooling, and the corresponding aqueous amine solutions were placed in the flask and the γ-BL was added dropwise at an internal temperature of 5° C. The yields were in each case determined as % by area by GC.

1a) Reaction of γ-BL with MMA
Starting materials: 65 ml (0.75 mol) of 40% strength MMA solution
  22 g (0.25 mol) of γ-BL
  Yield: >99.5% of N-methyl-γ-hydroxybutyramide
1b) Reaction of γ-BL with DMA
Starting materials: 95 ml (0.75 mol) of 40% strength DMA solution
  22 g (0.25 mol) of γ-BL
  Yield: >99.5% of N,N-dimethyl-γ-hydroxybutyramide
1c) Reaction of γ-BL with an MMA/DMA mixture
Starting materials: 65 ml (0.75 mol) of 40% strength MMA solution
  95 ml (0.75 mol) of 40% strength DMA solution
  44 g (0.5 mol) of γ-BL
  Yields: 76.3% of N-methyl-γ-hydroxybutyramide 23.6% of N,V-dimethyl-γ-hydroxybutyramide

Example 2

Reaction of γ-BL with MMA, DMA or TMA to give NMP

2a) Use of the Corresponding Aqueous Amine Solutions

The reactions were carried out in a 300 ml autoclave. The appropriate amine was firstly placed in the autoclave as an aqueous solution and γ-BL was slowly added; in each case, the corresponding amide (as described above) or in the case of TMA a corresponding internal salt (TMA-BL adduct) was formed in an exothermic reaction. After closing the autoclave, it was pressurized with 20 bar of $N_2$, heated to 255° C., maintained at this temperature for 3 hours and then allowed to cool again. The γ-BL conversions and the corresponding NMP yields were in each case determined as t by area by GC. Results:

| Experiment | Amine | unreacted γ-BL (%) | NMP yield (%) |
|---|---|---|---|
| 1 | MMA | 0.05 | 98.2 |
| 2 | DMA | 13.2 | 63.1 |
| 3 | TMA | 48.3 | 22.1 |

2b) Use of the Corresponding Anhydrous Amines

The reactions were carried out as described under 2a) in a 300 ml autoclave, with the amines in each case being condensed under pressure into the closed autoclave. After addition of γ-BL, the further procedure was as under 2a). Results:

| Experiment | Amine | unreacted γ-BL (%) | NMP yield (%) |
|---|---|---|---|
| 1 | MMA | 0 | 95 |
| 2 | DMA | 31.8 | 21.4 |
| 3 | TMA | 95.0 | 0.1 |

Example 3

Transalkylation of N,N-dimethyl-γ-hydroxybutyramide with MMA.

65 g (0.5 mol) of the dimethylamide and 86 ml of 40% strength aqueous MMA solution (1 mol) were placed in a 500 ml round-bottomed flask and heated at 80° C. for 1 hour. 7.6% of the corresponding monomethylamide were detected in the product.

Example 4

Reaction of γ-BL with an MMA/DMA Mixture 0.75 mol of MMA solution and 0.75 mol of DMA solution (each 40% strength in water) were placed in a round-bottomed flask and admixed with γ-BL at 50C with ice cooling. The solution was subsequently passed with a residence time of 10 minutes through a tube which was at 270° C. The products were in each case analyzed by GC (reported in % by area). Results:

| Temperature | corresponding monomethylamide (yield in %) | corresponding dimethylamide (yield in %) | NMP (yield in %) |
|---|---|---|---|
| 5° C. | 76.3 | 22.6 | 0 |
| 270° C. (10 min.) | 40.8 | 10.2 | 45 |

Example 5

Reaction of γ-BL with a Methylamine Mixture

Using a method analogous to Example 2, a mixture of 0.1 mol of MMA, 0.173 mol of DMA and 0.29 mol of TMA, in each case as 40% strength aqueous solution, was heated with 0.09 mol of γ-BL at 255° C. for 3 hours. The yield of NMP was 94.8% (0.0853 mol).

We claim:

1. A process for preparing N-methyl-2-pyrrolidone (NMP), which comprises preparing a mixture comprising monomethylamine, dimethylamine and trimethylamine and ammonia in a first process step by reacting ammonia with methanol at elevated temperature in the presence of an acid catalyst or a meal catalyst, separating off the ammonia, reacting the mixture comprising the methylamines with gamma-butyrolactone (γ-BL), in a molar ratio of monomethylamine to γ-BL of at least 1 in a second process step at elevated temperature and superatmospheric pressure, separating NMP and unreacted methylamines from the reaction product and returning unreacted methylamines to the first process step for reaction with methanol and ammonia.

2. A process as claimed in claim 1, wherein the reaction of the first process step is carried out continuously at from 300 to 500° C. and in the presence of a solid acid catalyst.

3. A process obtained in as claimed in claim 1, wherein the mixture obtained in the first process step after separating off ammonia has a content of the three methylamines, water and methanol of at least 96% by weight.

4. A process as claimed in claim 1, wherein the reaction of the second process step is carried out at from 200 to 300° C.

5. A process as claimed in claim 1, wherein the reaction of the second process step is carried out at a pressure of from 50 to 150 bar.

6. A process as claimed in claim 1, wherein the molar ratio of monomethylamine to γ-BL in the second process step is from 1.05 to 1.5.

7. A process as claimed in claim 1, wherein the reaction of the second process step is carried out continuously in a tube reactor at a residence time in the reactor of from 1.5 to 5 hours.

8. A process as claimed in claim 1, wherein the unreacted methylamines for return to the first process step are dimethylamine and trimethylamine.

* * * * *

UNITED STATES PATENT AND TRADEMARK OFFICE
CERTIFICATE OF CORRECTION

PATENT NO. : 6,348,601 B1
DATED : February 19, 2002
INVENTOR(S) : Ohlbach et al.

It is certified that error appears in the above-identified patent and that said Letters Patent is hereby corrected as shown below:

Title page,
ABSTRACT
Line 5, delete "10".

Signed and Sealed this

Twenty-third Day of April, 2002

Attest:

Attesting Officer

JAMES E. ROGAN
Director of the United States Patent and Trademark Office